United States Patent
Whitman

(10) Patent No.: US 6,843,403 B2
(45) Date of Patent: Jan. 18, 2005

(54) SURGICAL CLAMPING, CUTTING AND STAPLING DEVICE

(75) Inventor: Michael P. Whitman, New Hope, PA (US)

(73) Assignee: Power Medical Interventions, Inc., New Hope, PA (US)

(*) Notice: Subject to any disclaimer, the term of this patent is extended or adjusted under 35 U.S.C. 154(b) by 0 days.

(21) Appl. No.: 10/010,955

(22) Filed: Nov. 13, 2001

(65) Prior Publication Data

US 2002/0084304 A1 Jul. 4, 2002

Related U.S. Application Data

(63) Continuation-in-part of application No. 09/324,451, filed on Jun. 2, 1999, now Pat. No. 6,315,184.

(51) Int. Cl.$^7$ .............................................. A61H 17/068
(52) U.S. Cl. .................... 227/176.1; 227/19; 227/180.1; 606/219
(58) Field of Search ............................. 227/19, 176.1, 227/175.1, 178.1, 180.1

(56) References Cited

U.S. PATENT DOCUMENTS

| | | | |
|---|---|---|---|
| 1,831,250 A | | 11/1931 | Tomlinson |
| 3,079,606 A | | 3/1963 | Bobrov et al. |
| 3,193,165 A | | 7/1965 | Akhalaya et al. |
| 3,252,643 A | * | 5/1966 | Stekkopytov et al. ......... 227/19 |
| 3,256,875 A | | 6/1966 | Tsepelev et al. |
| 3,388,847 A | | 6/1968 | Kasulin et al. |

(List continued on next page.)

FOREIGN PATENT DOCUMENTS

| | | |
|---|---|---|
| DE | 2903159 | 7/1980 |
| DE | 3 300 768 | 7/1984 |
| DE | 4213426 | 10/1992 |
| DE | 4312147 | 10/1992 |
| EP | 0 116 220 | 8/1984 |
| EP | 0 121 474 | 10/1984 |

(List continued on next page.)

OTHER PUBLICATIONS

2002/0032451 A1 US Published patent application.
2002/0032452 A1 US Published patent application.
2002/0042620 A1 US Published patent application.
2002/0045888 A1 US Published patent application.
2002/0055795 A1 US Published patent application.
2002/0072736 A1 US Published patent application.
2001/031975 US Published patent application.
New York Magazine, Jun. 10, 2002. The Best Doctors in New York, p. 80 (in the form of a website archive printout).

*Primary Examiner*—Scott A. Smith
(74) *Attorney, Agent, or Firm*—Donald R. Piper, Jr.; Dann, Dorfman, Herrell & Skillman, P.C.

(57) ABSTRACT

A stapling device for use as an attachment to an electromechanical device driver comprises an upper jaw and a lower jaw, the upper jaw having staple guides corresponding to one or more staples in a removable staple tray disposed within a lower jaw, whereby a wedge having a threaded bore travels upon a matching threaded shaft in a channel disposed in the lower jaw behind the staple tray, such that rotation of the threaded shaft causes movement of the wedge through the channel while a sloped surface of the wedge contacts the staples to push the staples against the staples guides, closing the staples.

29 Claims, 9 Drawing Sheets

U.S. PATENT DOCUMENTS

| | | |
|---|---|---|
| 3,490,675 A | 1/1970 | Green et al. |
| 3,494,533 A | 2/1970 | Kasulin et al. |
| 3,552,626 A | 1/1971 | Astafiev |
| 3,568,659 A | 3/1971 | Karnegis |
| 3,618,842 A | 11/1971 | Bryan |
| 3,662,939 A | 5/1972 | Bryan |
| 3,815,476 A | 6/1974 | Green et al. |
| 3,858,577 A | 1/1975 | Bass et al. |
| 3,859,986 A | 1/1975 | Okada et al. |
| 3,952,748 A | 4/1976 | Kaliher et al. |
| 4,071,029 A | 1/1978 | Richmond et al. |
| 4,085,756 A | 4/1978 | Weaver |
| 4,198,960 A | 4/1980 | Utsugi |
| 4,198,982 A | 4/1980 | Former et al. |
| 4,202,479 A | 5/1980 | Razgulov et al. |
| 4,207,898 A * | 6/1980 | Becht .......................... 227/19 |
| 4,250,873 A | 2/1981 | Bonnet |
| 4,273,109 A | 6/1981 | Enderby |
| 4,273,111 A | 6/1981 | Tsykaya |
| 4,286,585 A | 9/1981 | Ogawa |
| 4,289,131 A | 9/1981 | Mueller |
| 4,289,133 A | 9/1981 | Rothfuss |
| 4,304,236 A | 12/1981 | Conta et al. |
| 4,310,115 A | 1/1982 | Inoue |
| 4,319,576 A | 3/1982 | Rothfuss |
| 4,334,539 A | 6/1982 | Childs et al. |
| 4,343,507 A | 8/1982 | Heuer et al. |
| 4,351,466 A | 9/1982 | Noiles |
| 4,367,729 A | 1/1983 | Ogiu |
| 4,379,457 A | 4/1983 | Gravener et al. |
| 4,402,311 A | 9/1983 | Hattori |
| 4,429,695 A | 2/1984 | Green |
| 4,442,964 A | 4/1984 | Becht |
| 4,445,509 A | 5/1984 | Auth |
| 4,445,892 A | 5/1984 | Hussein et al. |
| 4,448,188 A | 5/1984 | Loeb |
| 4,473,077 A | 9/1984 | Noiles et al. |
| 4,476,863 A | 10/1984 | Kanshin et al. |
| 4,485,817 A | 12/1984 | Swiggett |
| 4,487,270 A | 12/1984 | Huber |
| 4,488,523 A | 12/1984 | Shichman |
| 4,489,724 A | 12/1984 | Arnegger |
| 4,494,057 A | 1/1985 | Hotta |
| 4,494,549 A | 1/1985 | Namba et al. |
| 4,499,895 A | 2/1985 | Takayama |
| 4,505,272 A | 3/1985 | Utyamyshev et al. |
| 4,505,414 A | 3/1985 | Filipi |
| 4,520,817 A | 6/1985 | Green |
| 4,534,420 A | 8/1985 | Goldelius |
| 4,535,773 A | 8/1985 | Yoon |
| 4,559,928 A | 12/1985 | Takayama |
| 4,573,468 A | 3/1986 | Conta et al. |
| 4,574,806 A | 3/1986 | McCarthy |
| 4,576,167 A | 3/1986 | Noiles |
| 4,589,412 A | 5/1986 | Kensey |
| 4,589,582 A | 5/1986 | Bilotti |
| 4,592,354 A | 6/1986 | Rothfuss |
| 4,593,679 A | 6/1986 | Collins |
| 4,603,693 A | 8/1986 | Conta et al. |
| 4,605,001 A | 8/1986 | Rothfuss et al. |
| 4,606,343 A | 8/1986 | Conta et al. |
| 4,610,383 A | 9/1986 | Rothfuss et al. |
| D286,567 S | 11/1986 | Lichtman et al. |
| 4,631,052 A | 12/1986 | Kensey |
| 4,633,861 A | 1/1987 | Chow et al. |
| 4,633,874 A | 1/1987 | Chow et al. |
| 4,644,952 A | 2/1987 | Patipa et al. |
| 4,646,745 A | 3/1987 | Noiles |
| 4,655,673 A | 4/1987 | Hawkes |
| 4,667,673 A | 5/1987 | Li |
| 4,671,445 A | 6/1987 | Barker et al. |
| 4,672,961 A | 6/1987 | Davies |
| 4,674,515 A | 6/1987 | Andou et al. |
| 4,696,667 A | 9/1987 | Masch |
| 4,700,703 A | 10/1987 | Resnick et al. |
| 4,703,887 A | 11/1987 | Clanton et al. |
| 4,705,038 A | 11/1987 | Sjostrom et al. |
| 4,708,141 A | 11/1987 | Inoue et al. |
| 4,732,156 A | 3/1988 | Nakamura |
| 4,733,118 A | 3/1988 | Mihalko |
| 4,742,815 A | 5/1988 | Ninan et al. |
| 4,752,024 A | 6/1988 | Green et al. |
| 4,754,909 A | 7/1988 | Barker et al. |
| 4,756,309 A | 7/1988 | Sachse et al. |
| 4,760,840 A | 8/1988 | Fournier, Jr. et al. |
| 4,771,774 A | 9/1988 | Simpson et al. |
| 4,776,506 A | 10/1988 | Green |
| 4,781,186 A | 11/1988 | Simpson et al. |
| 4,784,137 A | 11/1988 | Kulik et al. |
| 4,805,823 A | 2/1989 | Rothfuss |
| 4,813,928 A | 3/1989 | Abet et al. |
| 4,815,469 A | 3/1989 | Cohen et al. |
| 4,817,847 A | 4/1989 | Redtenbacher et al. |
| 4,819,632 A | 4/1989 | Davies |
| 4,867,158 A | 9/1989 | Sugg |
| 4,869,415 A | 9/1989 | Fox |
| 4,873,977 A | 10/1989 | Avant et al. |
| 4,887,599 A | 12/1989 | Muller |
| 4,890,602 A | 1/1990 | Hake |
| 4,892,244 A | 1/1990 | Fox et al. |
| 4,893,613 A | 1/1990 | Hake |
| 4,893,622 A | 1/1990 | Green et al. |
| 4,903,697 A | 2/1990 | Resnick et al. |
| 4,907,591 A | 3/1990 | Vasconcellos et al. |
| 4,907,973 A | 3/1990 | Hon |
| 4,917,114 A | 4/1990 | Green et al. |
| 4,928,699 A | 5/1990 | Sasai |
| 4,930,494 A | 6/1990 | Takehana et al. |
| 4,936,845 A | 6/1990 | Stevens |
| 4,941,454 A | 7/1990 | Wood et al. |
| 4,955,882 A | 9/1990 | Hakky |
| 4,957,499 A | 9/1990 | Lipatov et al. |
| 4,962,877 A | 10/1990 | Hervas |
| 4,976,688 A | 12/1990 | Rosenblaum |
| 4,976,710 A | 12/1990 | Mackin |
| 4,978,049 A | 12/1990 | Green |
| 4,982,726 A | 1/1991 | Taira |
| 4,994,060 A | 2/1991 | Rink et al. |
| 4,995,877 A | 2/1991 | Ams et al. |
| 5,005,749 A | 4/1991 | Aranyi |
| 5,040,715 A | 8/1991 | Green et al. |
| 5,059,203 A | 10/1991 | Husted |
| 5,065,929 A | 11/1991 | Schulze et al. |
| D322,143 S | 12/1991 | Spreckelmeier |
| 5,071,430 A | 12/1991 | de Salis et al. |
| 5,077,506 A | 12/1991 | Krause |
| 5,104,025 A | 4/1992 | Main et al. |
| 5,129,570 A | 7/1992 | Schulze et al. |
| 5,133,359 A | 7/1992 | Kedem |
| 5,133,713 A | 7/1992 | Huang et al. |
| 5,133,729 A | 7/1992 | Sjostrom |
| 5,139,513 A | 8/1992 | Segato |
| 5,170,925 A | 12/1992 | Madden et al. |
| 5,171,247 A | 12/1992 | Hughett et al. |
| 5,171,251 A | 12/1992 | Bregen et al. |
| 5,173,133 A | 12/1992 | Morin et al. |
| 5,192,292 A | 3/1993 | Cezana et al. |
| 5,197,649 A | 3/1993 | Bessler et al. |
| 5,201,325 A | 4/1993 | McEwen et al. |
| 5,201,750 A | 4/1993 | Hocherl et al. |

| Patent No. | Date | Inventor(s) |
|---|---|---|
| 5,205,459 A | 4/1993 | Brinkerhoff et al. |
| 5,207,691 A | 5/1993 | Nardella |
| 5,207,697 A | 5/1993 | Carusillo et al. |
| 5,217,003 A | 6/1993 | Wilk |
| 5,221,279 A | 6/1993 | Cook et al. |
| 5,224,951 A | 7/1993 | Freitas |
| 5,226,426 A | 7/1993 | Yoon |
| 5,237,884 A | 8/1993 | Seto |
| 5,249,583 A | 10/1993 | Mallaby |
| 5,258,007 A | 11/1993 | Spetzler et al. |
| 5,258,008 A | 11/1993 | Wilk |
| 5,261,877 A | 11/1993 | Fine et al. |
| 5,267,997 A | 12/1993 | Farin et al. |
| 5,268,622 A | 12/1993 | Philipp |
| 5,271,543 A | 12/1993 | Grant et al. |
| 5,271,544 A | 12/1993 | Fox et al. |
| RE34,519 E | 1/1994 | Fox et al. |
| 5,275,322 A | 1/1994 | Brinkerhoff et al. |
| 5,275,323 A | 1/1994 | Schulze et al. |
| 5,279,565 A | 1/1994 | Klein et al. |
| 5,285,945 A | 2/1994 | Brinkerhoff et al. |
| 5,289,963 A | 3/1994 | McGarry et al. |
| 5,290,299 A | 3/1994 | Fain et al. |
| 5,292,053 A | 3/1994 | Bilotti et al. |
| 5,307,976 A | 5/1994 | Olson et al. |
| 5,312,023 A | 5/1994 | Green et al. |
| 5,314,436 A | 5/1994 | Wilk |
| 5,318,221 A | 6/1994 | Green et al. |
| 5,326,013 A | 7/1994 | Green et al. |
| 5,330,486 A | 7/1994 | Wilk |
| 5,333,773 A | 8/1994 | Main et al. |
| 5,342,299 A | 8/1994 | Snoke et al. |
| 5,342,382 A | 8/1994 | Brinkerhoff et al. |
| 5,344,420 A | 9/1994 | Hilal et al. |
| 5,350,104 A | 9/1994 | Main et al. |
| 5,354,266 A | 10/1994 | Snoke |
| 5,358,506 A | 10/1994 | Green et al. |
| 5,364,001 A | 11/1994 | Bryan |
| 5,368,015 A | 11/1994 | Wilk |
| 5,368,607 A | 11/1994 | Freitas |
| 5,380,321 A | 1/1995 | Yoon |
| 5,383,880 A | 1/1995 | Hooven |
| 5,395,030 A * | 3/1995 | Kuramoto et al. ............ 227/19 |
| 5,395,033 A | 3/1995 | Byrne et al. |
| 5,397,046 A | 3/1995 | Savage et al. |
| 5,400,267 A | 3/1995 | Denen et al. |
| D357,535 S | 4/1995 | Grant et al. |
| 5,403,312 A | 4/1995 | Yates et al. |
| 5,403,326 A | 4/1995 | Harrison et al. |
| 5,403,327 A | 4/1995 | Thornton et al. |
| 5,411,508 A | 5/1995 | Bessler et al. |
| 5,413,267 A | 5/1995 | Solyntjes |
| 5,413,268 A | 5/1995 | Green et al. |
| 5,415,334 A | 5/1995 | Williamson et al. |
| 5,425,738 A | 6/1995 | Gustafson et al. |
| 5,425,745 A | 6/1995 | Green et al. |
| 5,431,322 A | 7/1995 | Green et al. |
| 5,431,645 A | 7/1995 | Smith et al. |
| 5,433,721 A * | 7/1995 | Hooven et al. .......... 227/180.1 |
| 5,437,636 A | 8/1995 | Snoke et al. |
| 5,437,684 A | 8/1995 | Calabrese et al. |
| 5,441,507 A | 8/1995 | Wilk |
| 5,443,198 A | 8/1995 | Viola et al. |
| 5,454,825 A | 10/1995 | Van Leeuwen et al. |
| 5,460,182 A | 10/1995 | Goodman et al. |
| 5,467,911 A | 11/1995 | Tsuruta et al. |
| 5,472,132 A | 12/1995 | Savage et al. |
| 5,474,223 A | 12/1995 | Viola et al. |
| 5,476,206 A | 12/1995 | Green et al. |
| 5,482,197 A | 1/1996 | Green et al. |
| 5,485,947 A | 1/1996 | Olson et al. |
| 5,487,499 A | 1/1996 | Sorrentino et al. |
| 5,487,500 A | 1/1996 | Knodel et al. |
| 5,496,269 A | 3/1996 | Snoke |
| 5,518,163 A | 5/1996 | Hooven |
| 5,518,164 A | 5/1996 | Hooven |
| 5,524,180 A | 6/1996 | Wang et al. |
| 5,529,235 A | 6/1996 | Boiarski et al. |
| 5,531,687 A | 7/1996 | Snoke et al. |
| 5,533,661 A | 7/1996 | Main et al. |
| 5,549,565 A | 8/1996 | Ryan et al. |
| 5,553,765 A | 9/1996 | Knodel et al. |
| 5,554,169 A | 9/1996 | Green et al. |
| 5,562,702 A | 10/1996 | Huitema et al. |
| 5,571,116 A | 11/1996 | Bolanos et al. |
| 5,582,611 A | 12/1996 | Tsuruta et al. |
| 5,584,425 A | 12/1996 | Savage et al. |
| 5,588,579 A | 12/1996 | Schnut et al. |
| 5,591,186 A | 1/1997 | Wurster et al. |
| 5,597,107 A | 1/1997 | Knodel et al. |
| 5,599,347 A | 2/1997 | Hart et al. |
| 5,609,285 A | 3/1997 | Grant et al. |
| 5,609,560 A | 3/1997 | Ichikawa et al. |
| 5,617,857 A | 4/1997 | Chader et al. |
| 5,639,008 A | 6/1997 | Gallagher et al. |
| 5,651,780 A | 7/1997 | Jackson et al. |
| 5,653,374 A | 8/1997 | Young et al. |
| 5,662,259 A * | 9/1997 | Yoon ...................... 227/176.1 |
| 5,662,673 A | 9/1997 | Kieturakis |
| 5,667,517 A | 9/1997 | Hooven |
| 5,676,674 A | 10/1997 | Bolanos et al. |
| 5,693,031 A | 12/1997 | Ryan et al. |
| 5,709,335 A | 1/1998 | Heck |
| 5,732,872 A | 3/1998 | Bolduc et al. |
| 5,735,861 A | 4/1998 | Peifer et al. |
| 5,749,893 A | 5/1998 | Vidal et al. |
| 5,758,814 A | 6/1998 | Gallagher et al. |
| 5,762,458 A | 6/1998 | Wang et al. |
| 5,772,597 A | 6/1998 | Golderberger et al. |
| 5,779,130 A | 7/1998 | Alesi et al. |
| 5,782,396 A | 7/1998 | Mastri et al. |
| 5,782,397 A | 7/1998 | Koukline |
| 5,792,135 A | 8/1998 | Madhani et al. |
| 5,797,835 A | 8/1998 | Green |
| 5,797,900 A | 8/1998 | Madhani et al. |
| 5,797,944 A | 8/1998 | Nobles et al. |
| 5,807,377 A | 9/1998 | Madhani et al. |
| 5,814,044 A | 9/1998 | Hooven |
| 5,815,640 A | 9/1998 | Wang et al. |
| 5,817,113 A | 10/1998 | Gifford, III et al. |
| 5,836,503 A | 11/1998 | Ehrenfels et al. |
| 5,846,221 A | 12/1998 | Snoke et al. |
| 5,855,583 A | 1/1999 | Wang et al. |
| 5,857,996 A | 1/1999 | Snoke |
| 5,860,953 A | 1/1999 | Snoke et al. |
| 5,868,760 A | 2/1999 | McGuckin, Jr. |
| 5,871,471 A | 2/1999 | Ryan et al. |
| 5,878,193 A | 3/1999 | Wang et al. |
| 5,881,943 A | 3/1999 | Heck et al. |
| 5,897,562 A | 4/1999 | Bolanos et al. |
| 5,907,664 A | 5/1999 | Wang et al. |
| 5,915,616 A | 6/1999 | Viola et al. |
| 5,925,055 A | 7/1999 | Adrian et al. |
| 5,931,848 A | 8/1999 | Saaadat |
| 5,947,363 A | 9/1999 | Bolduc et al. |
| 5,951,549 A | 9/1999 | Richardson et al. |
| 5,954,259 A | 9/1999 | Viola et al. |
| 5,957,363 A | 9/1999 | Heck |
| 5,957,882 A | 9/1999 | Nita et al. |
| 5,957,884 A | 9/1999 | Hooven |
| 5,976,159 A | 11/1999 | Bolduc et al. |

| | | |
|---|---|---|
| 5,984,919 A | 11/1999 | Hilal et al. |
| 5,989,274 A | 11/1999 | Davison et al. |
| 5,993,378 A | 11/1999 | Lemelson |
| 5,993,454 A | 11/1999 | Longo |
| 5,997,510 A | 12/1999 | Schwwemberger |
| 6,001,108 A | 12/1999 | Wang et al. |
| 6,004,335 A | 12/1999 | Vaitekunas et al. |
| 6,007,512 A | 12/1999 | Hooven |
| 6,007,531 A | 12/1999 | Snoke et al. |
| 6,010,493 A | 1/2000 | Snoke |
| 6,017,322 A | 1/2000 | Snoke et al. |
| 6,017,354 A | 1/2000 | Culp et al. |
| 6,059,719 A | 5/2000 | Yamamoto et al. |
| 6,063,095 A | 5/2000 | Wang et al. |
| 6,068,627 A | 5/2000 | Drszulak et al. |
| 6,074,402 A | 6/2000 | Peifer et al. |
| 6,083,163 A | 7/2000 | Wegner et al. |
| 6,083,627 A | 7/2000 | Kenny et al. |
| 6,086,600 A | 7/2000 | Kortenbach |
| 6,090,120 A | 7/2000 | Wright et al. |
| 6,099,466 A | 8/2000 | Sano et al. |
| 6,106,512 A | 8/2000 | Cochran et al. |
| 6,119,913 A * | 9/2000 | Adams et al. ............ 227/178.1 |
| 6,126,058 A | 10/2000 | Adams et al. |
| 6,126,591 A | 10/2000 | McGarry et al. |
| 6,132,368 A | 10/2000 | Cooper |
| 6,165,169 A | 12/2000 | Panescy et al. |
| 6,174,324 B1 | 1/2001 | Egan et al. |
| 6,179,837 B1 | 1/2001 | Hooven |
| D438,617 S | 3/2001 | Cooper et al. |
| 6,201,984 B1 | 3/2001 | Funda et al. |
| 6,206,903 B1 | 3/2001 | Rramans |
| D441,076 S | 4/2001 | Cooper et al. |
| D441,862 S | 5/2001 | Cooper et al. |
| 6,244,809 B1 | 6/2001 | Wang et al. |
| 6,246,200 B1 | 6/2001 | Blumenkrantz et al. |
| D444,555 S | 7/2001 | Cooper et al. |
| 6,264,087 B1 | 7/2001 | Whitman |
| 6,308,089 B1 | 10/2001 | von der Ruhr et al. |
| 6,309,397 B1 | 10/2001 | Julian et al. |
| 6,312,435 B1 | 11/2001 | Wallace et al. |
| 6,315,184 B1 * | 11/2001 | Whitman ................ 227/180.1 |
| 6,331,181 B1 | 12/2001 | Tierney et al. |
| 6,346,072 B1 | 2/2002 | Cooper |
| 6,364,888 B1 | 4/2002 | Niemeyer et al. |
| 6,371,952 B1 | 4/2002 | Madhani et al. |
| 6,394,998 B1 | 5/2002 | Wallace et al. |
| 6,398,726 B1 | 6/2002 | Ramans et al. |
| 6,434,507 B1 | 8/2002 | Clayton et al. |
| 6,443,973 B1 | 9/2002 | Whitman |
| 6,491,201 B1 | 12/2002 | Whitman |
| 6,491,701 B2 | 12/2002 | Tierney et al. |
| 6,517,565 B1 | 2/2003 | Whitman |
| 6,616,446 B1 | 9/2003 | Schmid |
| 6,716,233 B1 | 4/2004 | Whitman |
| 2002/0032452 A1 | 3/2002 | Tierney et al. |
| 2002/0042620 A1 | 4/2002 | Julian et al. |
| 2002/0045888 A1 | 4/2002 | Ramans et al. |
| 2002/0055795 A1 | 5/2002 | Niemeyer et al. |
| 2002/0072736 A1 | 6/2002 | Tierney et al. |

FOREIGN PATENT DOCUMENTS

| | | |
|---|---|---|
| EP | 0 156 774 | 10/1985 |
| EP | 0 216 532 | 4/1987 |
| EP | 0 399 701 | 5/1990 |
| EP | 0 539 762 | 10/1992 |
| EP | 0 514 139 | 11/1992 |
| EP | 0 552050 | 1/1993 |
| EP | 0 552 050 | 1/1993 |
| EP | 0 536 903 | 4/1993 |
| EP | 0 593 920 | 9/1993 |
| EP | 0 621006 | 3/1994 |
| EP | 0 621 006 | 3/1994 |
| EP | 0 598 579 | 5/1994 |
| EP | 0 634 144 | 1/1995 |
| EP | 0 705 571 | 4/1996 |
| EP | 0 947 167 | 10/1999 |
| EP | 0 653 922 | 12/1999 |
| FR | 2660851 | 10/1991 |
| GB | 2044108 | 10/1980 |
| GB | 2 180 455 | 4/1987 |
| NL | 7 711 347 | 4/1979 |
| RU | 659146 | 4/1979 |
| WO | 82/03545 | 10/1982 |
| WO | 83/00992 | 3/1983 |
| WO | 90/05491 | 5/1990 |
| WO | 91/07136 | 5/1991 |
| WO | 92/16141 | 10/1992 |
| WO | 93/08754 | 5/1993 |
| WO | 93/14706 | 8/1993 |
| WO | 95/18572 | 7/1995 |
| WO | 95/35065 | 12/1995 |
| WO | 98/14129 | 4/1998 |
| WO | 98/141129 | 4/1998 |
| WO | 99/20328 | 4/1999 |
| WO | 99/58076 | 11/1999 |
| WO | 00/72762 | 12/2000 |
| WO | 00/72765 | 12/2000 |
| WO | 01/08572 | 2/2001 |
| WO | 01/62163 | 8/2001 |

* cited by examiner

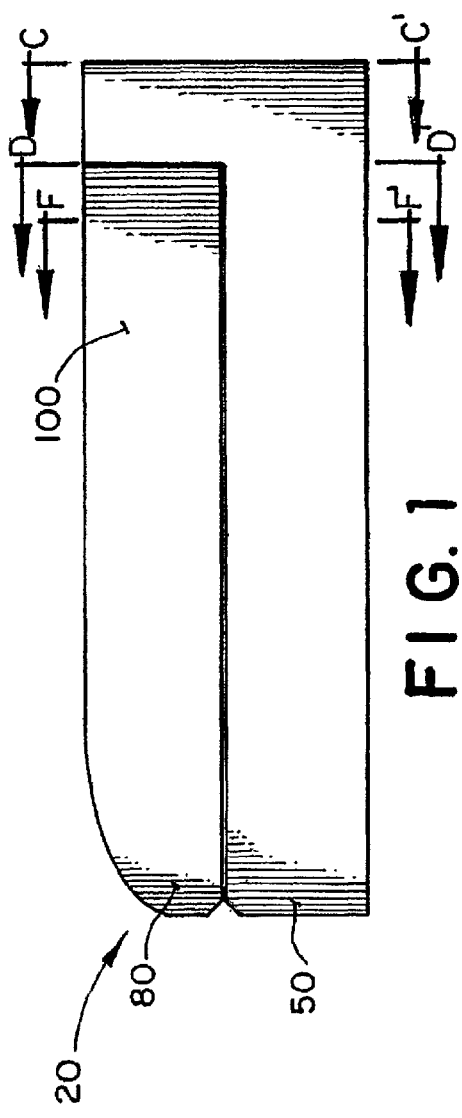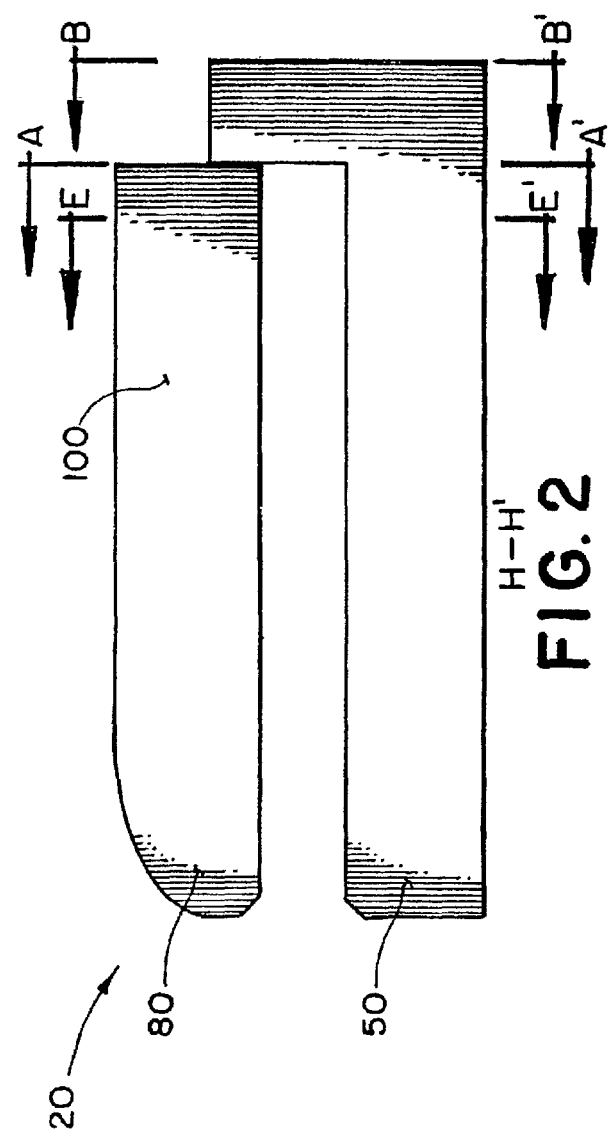

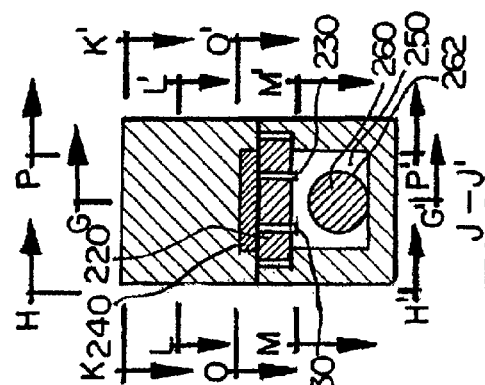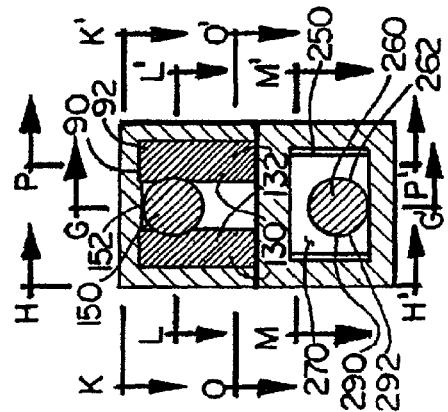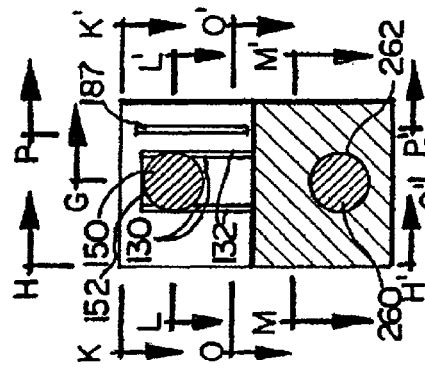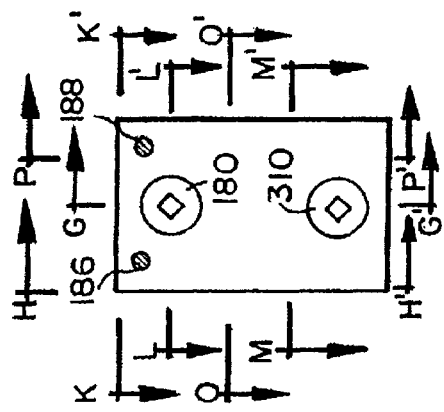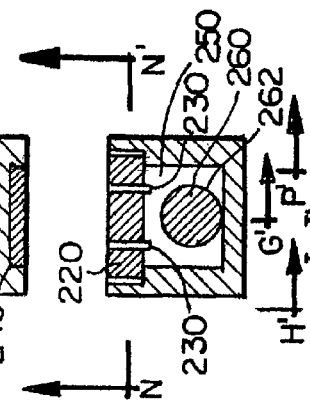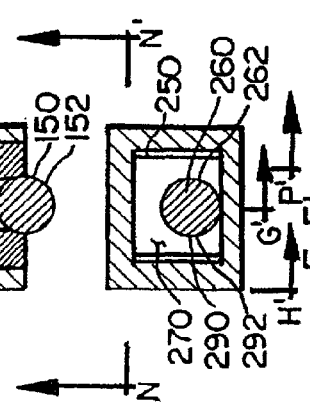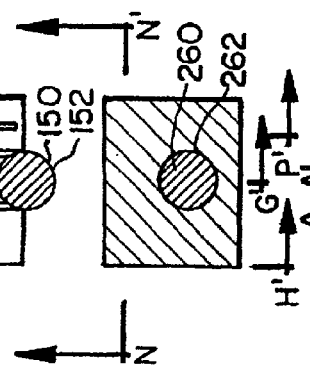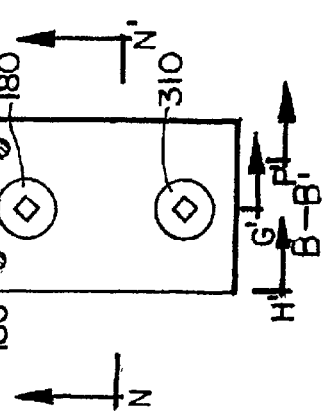

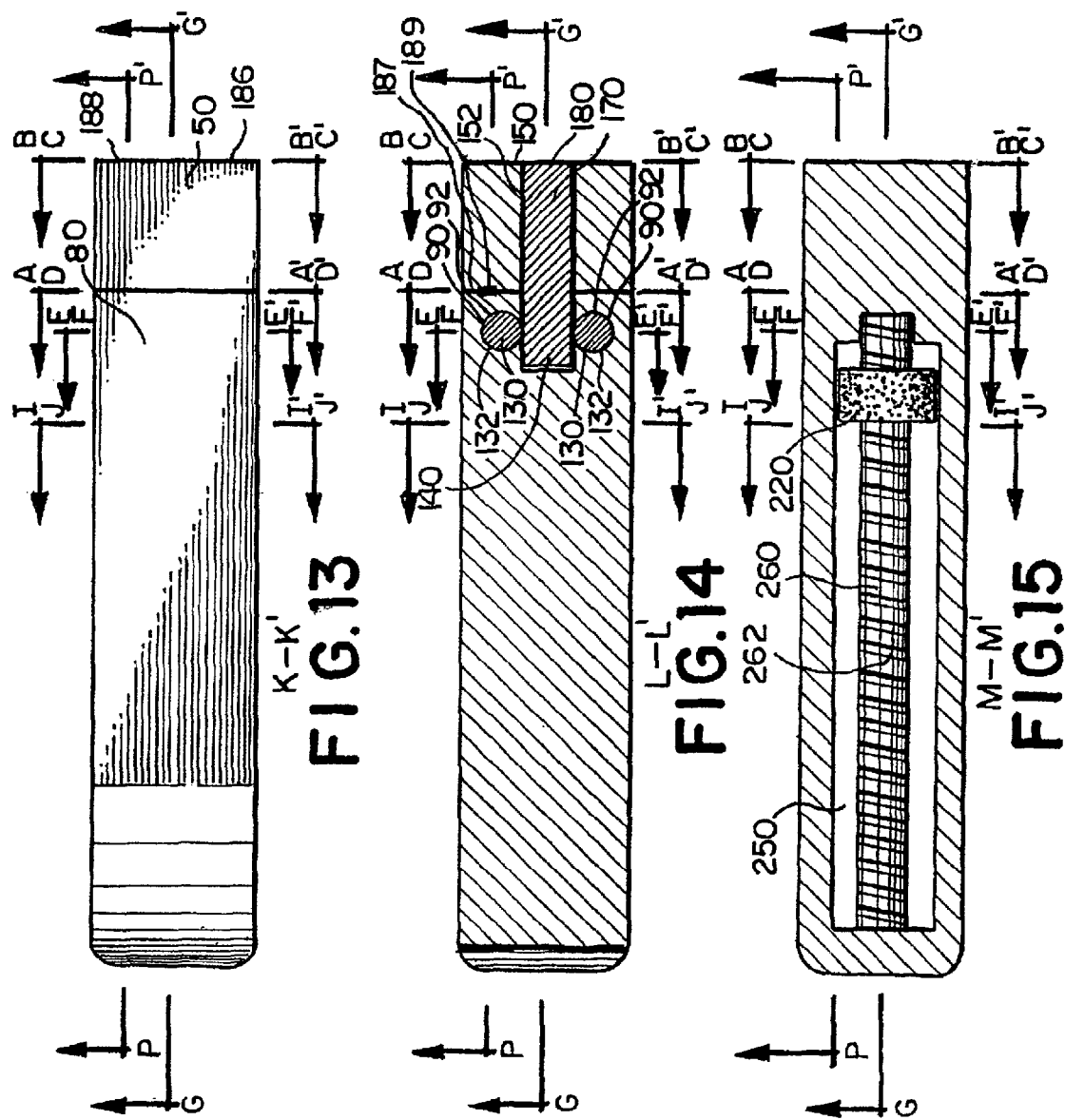

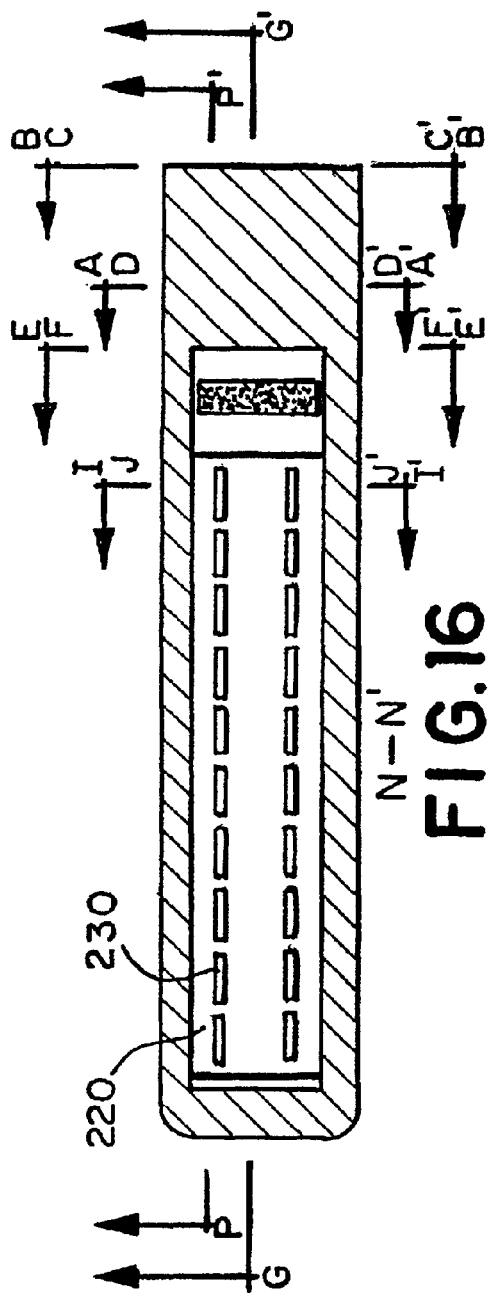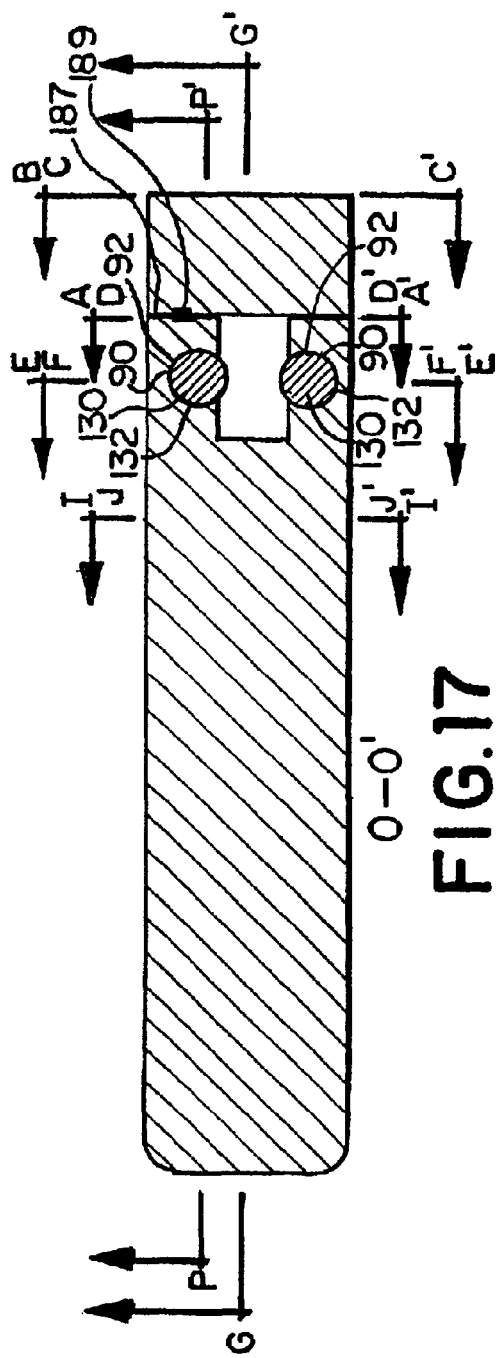

SURGICAL CLAMPING, CUTTING AND STAPLING DEVICE

This application is a continuation-in-part of application Ser. No. 09/324,451, now U.S. Pat. No. 6,315,184 entitled "A Stapling Device for Use with an Electromechanical Driver Device for Use with Anastomosing, Stapling, and Resecting Instruments", filed on Jun. 2, 1999, which is incorporated herein by reference.

BACKGROUND OF THE INVENTION

1. Field of the Invention

The present invention relates generally to an electromechanical device for use with anastomosing, stapling, and resecting surgical tools, and more specifically to a stapling device which can be attached to and serve as an extension of an electromechanical device driver, to enable the stapling together of colon and other tissue.

2. Description of the Prior Art

Upon identification of cancerous and other anomalous tissue in the gastrointestinal tract, surgical intervention is often prescribed. The field of cancer surgery, and more specifically, the surgical procedure by which a section of the gastrointestinal tract which includes cancerous tissue is resected includes a number of uniquely designed instruments. In combination with a description of the present instrumentation and their functions, a description of the state of the art in this surgical procedure shall also be provided.

The first question which must be answered when determining how to treat gastrointestinal tract cancer relates to the specific location of the cancerous tissue. This is very important insofar as the instruments which are provided in the present art have limitations relating to how far they may be inserted into the gastrointestinal tract. If the cancerous tissue is too far up or down the gastrointestinal tract, then the standard instrumentation provided is unusable, thus requiring special accommodations. These accommodations generally increase the risk of contamination of the surrounding tissues with bowel contents, increase the length of the surgery and the corresponding need for anesthesia, and eliminate the benefits of precise anastomosing and stapling which comes from utilizing a mechanized device.

More specifically, in the event that the cancerous tissue is located at a position in the colon which is accessible by the present instrumentation, the patient's abdomen is initially opened to expose the bowel. The surgeon then cuts the tube of the colon on either side of the cancerous tissue, while simultaneously stapling closed the two open ends of the bowel (a distal end which is directed toward the anus, and the proximal end which is closest to the lower intestine). This temporary closure is performed in order to minimize contamination. The linear cutter and stapling instrument which is used in the prior art is provided in a perspective view in FIG. 19.

More particularly, this temporary closure is achieved when the colon is placed between the scissoring elements at the tip of the linear cutter and stapling instrument. By squeezing the trigger in the handle of the device, the surgeon causes the scissoring elements to come together. A second trigger (or a secondary action of the same trigger) is then actuated to drive a series of staples and a cutting blade through the clamped end of the colon, thereby closing and transecting the ends.

After the sealing of the two exposed distal and proximal ends, the surgeon creates a small opening in the proximal end of the bowel and inserts the removable anvil portion of an anastomosing and stapling instrument. This step, as well as those of the remainder of the surgical procedure, are related to the functioning of this surgical instrument which is provided in a perspective view in FIG. 20. More particularly, the surgeon begins by taking the instrument and manually turning the dial at the base of the handle which causes the anvil head at the opposite end to advance forward. The surgeon continues to turn the dial until the anvil head advances to its most extreme extended position. This manual turning requires nearly thirty full rotations. Once fully extended, the anvil head of the instrument is decoupled therefrom and is inserted into the exposed proximal end such that the coupling post extends outwardly therethrough. As described above, this proximal end is then stapled closed. The extending shaft of the anastomosing and stapling instrument is then inserted and advanced into the lower colon, transanally, until the coupling stem thereof extends through the stapled distal end. The surgeon then joins the coupling ends of the anvil and shaft together and begins to manually rotate the dial in the handle again, this time bringing the anvil head closer to the tip of the shaft.

Once the anvil head and shaft are brought close together, after the surgeon has manually rotated the dial another thirty times, a grip-style trigger in the handle is manually actuated. This actuation causes a circular blade to advance axially out from the tip of the shaft, and into contact with the opposing face of the anvil. The blade cuts through the stapled-closed ends of the proximal and distal ends of the colon, thereby also cutting a new pair of ends of the proximal and distal portions of the colon. The tissue which has been severed is held in an interior volume at the end of the shaft. In lock step with the cutting, the freshly opened ends are joined together by a series of staples which are advanced through holes in the perimeter of the tip of the shaft (being pressed against and closed by the opposing face of the anvil). The coupled shaft and anvil are then withdrawn from the patient.

More particularly with respect to the structural features of the linear stapling instrument of the prior art which is provided in FIG. 19, the device comprises a pistol grip-styled structure having an elongate shaft and distal portion. The distal portion includes a pair of scissors-styled gripping elements which clamp the open ends of the colon closed. In fact only one of the two scissors-styled gripping elements, the anvil portion, moves (pivots) relative to overall structure; the other remains fixed. The actuation of this scissoring means (the pivoting of the anvil portion) is controlled by means of a grip trigger maintained in the handle. A number of different means have been disclosed for holding the tips of the scissoring arms closed, including snaps, clips, collars, et al.

In addition to the scissoring means, the distal portion also includes a stapling mechanism. The non-moving element of the scissoring mechanism includes a staple cartridge receiving region and a mechanism for driving the staples up through the clamped end of the colon, against the anvil portion, thereby sealing the previously opened end. The scissoring elements may be integrally formed with the shaft, or may be detachable such that various scissoring and stapling elements may be interchangeable. More particularly with respect to the structural features of the anastomosing and stapling instrument of the prior art which is provided in FIG. 20, the device comprises an anvil portion, a staple, blade and reservoir portion, a shaft portion, and a handle portion. The anvil portion, which is selectively removable from the tip of the shaft, is bullet shaped, having a blunt nosed top portion, a flat cutting support surface on the bottom, and a coupling post extending axially from the bottom surface.

The staple, blade, and reservoir portion (SBR portion) of the instrument is provided at the distal end of the instrument, and includes a selectively advanceable and retractable coupling stem for selectively receiving thereon the anvil portion. This action of the coupling stem is provided by a screw threaded shaft and worming mechanism mounted in the handle (described more fully below). The SBR portion is cylindrical in shape, forming a housing which has a hollow interior. It is this hollow interior which forms the reservoir. The blade is similarly cylindrical, and seats in the inside of the housing, against the inner wall thereof. The blade is selectively advanceable axially outward from the housing, in accordance with actuation of a trigger mechanism of the handle (again, described more fully below). On the axially outward facing surface of the cylindrical wall of the housing are a series of staple ports, through which the staples of the device are discharged. The same actuation which drives the blade forward similarly drives a series of staple drivers forward within the cylindrical walls. More accurately, the staple driver is a cylindrical component which has a series of protuberances on the axial end thereof, the protuberances being positioned in accordance with the distribution of staples and holes. The staples, prior to being discharged, are mounted in the holes; and they are advanced through the holes by the action of the staple driver and the protuberances thereof.

The shaft portion of the instrument is a simple rigid extended structure which is intended as a sheath for a pair of elongate rods. The first rod is coupled to the worming mechanism introduced above, and described more fully below with respect to the handle portion, and is the means by which the anvil portion and the coupling stem of the SBR portion are selectively advanced and retracted. The second rod is coupled to the trigger of the handle at one end (also introduced above, and described more fully below) and to the blade and staple driver at the other end. The sheath protects the patient and the instrument when it is advanced into the colon transanally. The nature of the actuation mechanisms however, requires that the shaft be rigid. This rigidity limits the length of the shaft; and combination, i.e. the length and rigidity of the instrument, these features limit the sections of the colon which may be treated using this device.

The handle of this instrument of the prior art comprises a pistol grip styled structure having a turning dial at the butt (i.e. the end opposing the junction of the shaft portion with the handle) and a finger actuated trigger. The trigger includes a safety mechanism which physically prevents actuation unless moved out of the interference position. The turning dial is actionably coupled to a worming mechanism which is used to advance the first rod of the shaft portion (thereby advancing the coupling stem and the anvil). The trigger functions as a basic lever to push the second rod forward within the shaft, thereby advancing the blade and staple driver.

As with many such devices of the prior art, all of these devices are considered fully disposable, and are, in fact, thrown away after a single use. They are complicated devices, having multiple moving parts, requiring substantial structural integrity and, therefore, expense in manufacturing. The fact that they are used only once, and no part can be used again, renders the use of such devices expensive and wasteful of resources.

In addition to this failure, as can be readily observed from the preceding descriptions, the prior art devices suffer from numerous other limitations which would be desirable to overcome. These include the rigid and limited length shaft of the anastomosing and stapling instrument (which limits the portion of the gastrointestinal tract which may be treated by such a device), as well as the requirement that the surgeon manually actuate a number of different functions (including those associated with the dial and trigger of the anastomosing and stapling instrument and the multiple triggers of the cutting and stapling instrument).

Therefore, it is a principal object of the present invention to provide an instrument for stapling gastrointestinal tissue during colon surgery, which reduces the waste of resources by permitting use as an attachment to an electromechanical device driver.

It is a also a principal object of the present invention to provide an instrument which alerts the surgeon when conditions are safe and/or appropriate for the surgeon to begin the stapling procedure.

It is further an object of the present invention to provide an instrument assembly which reduces the requirements for the surgeon to manually actuate different components and mechanisms.

It is further an object of the present invention to provide a stapling mechanism that can be integrated with other electromechanical devices into an attachment for use with an electromechanical device driver.

Other objects of the present invention shall be recognized in accordance with the description thereof provided hereinbelow, and in the Detailed Description of the Preferred Embodiments in conjunction with the remaining Figures.

SUMMARY OF THE INVENTION

The preceding objects of the invention are provided by virtue of an electromechanical stapling device which is actuateable by and once coupled to an electromechanical device driver. It should be recognized that this electromechanical stapling device can be used in conjunction with a linear clamping mechanism as described above and in the Detailed Description of the Preferred Embodiments below. More particularly, the linear clamping mechanism of the attachment is used to first clamp the open end of a colon, and then the stapling mechanism of the present invention is used to staple and transect the colon tissue together in one motion.

More particularly, the present invention can be used in a system comprising three components, which are (1) an electromechanical driver, (2) a linear clamping, cutting and stapling attachment, and (3) an anastomosing and stapling attachment, the latter two attachments having a common designed coupling interface which joins with the driver component. First, with respect to the electromechanical driver, the driver has a handle and a flexible drive shaft. The handle has a pistol grip-styled design, having a pair of finger triggers which are independently coupled to separate motors which each turn separate flexible drive shafts (described more fully, hereinbelow). The motors are each dual direction motors, and are coupled to a manual drive switch mounted to the top of the handle, by which the user can selectively alter the turning direction of each motor. This dual direction capacity may be most simply achieved by selecting motors which turn in a direction corresponding to the direction of current, and actuation of the drive switches alters the direction of the current accordingly. In this example, the power source supplying the motors must be a direct current source, such as a battery pack (and most desirably, a rechargeable battery pack). In the event that the device should be useable with an alternating current, either a transformer can be included, or a more sophisticated intermediate gearing assembly may be provided. In conjunction with the present description, the embodiments of the present invention which will be described utilize a rechargeable battery pack providing a direct current.

In addition to the motor components, the handle further includes several other features, including: (1) a remote status indicator; (2) a shaft steering means; and (3) at least one additional electrical supply. First, the remote status indicator may comprise an LCD (or similar read out device) by which the user may gain knowledge of the position of components (for example whether a clamping element is in the proper position prior to the driving of the staples). Second, the handle also includes a manually actuateable steering means, for example, a joystick or track ball, for directing the movement of the flexible shaft (by means of guidewires implanted in the shaft portion described more fully hereinbelow). Finally, the handle may include an additional electrical power supply and an on off switch for selectively supplying electrical power to the attachments.

More particularly, with respect to the flexible shaft, the shaft comprises a tubular sheath, preferably formed of a simple elastomeric material which is tissue compatible and which is sterilizable (i.e. is sufficiently rugged to withstand an autoclave). Various lengths of this shaft may be provided in conjunction with the present invention. In this case, the flexible shaft and the handle portions should be separable. If separable, the interface between the proximal end of the shaft and the distal end of the handle should include a coupling means for the drive components. Specifically regarding the drive components of the shaft, within the elastomeric sheath are a pair of smaller fixed tubes which each contain a flexible drive shaft which is capable of rotating within the tube. The flexible drive shaft, itself, simply must be capable of translating a torque from the motor in the handle to the distal end of the shaft, while still being flexible enough to be bent, angled, curved, etc. as the surgeon deems necessary to "snake" through the colon of the patient. For example, the drive shafts may comprise a woven steel fiber cable. It shall be recognized that other drive shafts may be suitable for this purpose. In order for the distal end of the drive shaft to couple with an attachment, such as the clamping and stapling device of the present invention (as described more fully below), however, the distal tips of the drive shafts must have a conformation which permits the continued translation of torque. For example, the distal tips of the drive shafts may be hexagonal, thereby fitting into a hexagonal recess in the coupling interface of the attachment. As suggested above, in conjunction with the manually actuateable steering means mounted to the handle, the sheath further includes at least two guidewires which are flexible, but are coupled to the inner surface of the sheath near the distal end thereof. The guidewires may be axially translated relative to one another by actuation of the steering means, which action causes the sheath to bend and curve accordingly. Also as suggested above, in conjunction with the LCD indicator of the handle, the shaft further contains an electrical lead for coupling to the attachments. This electrical lead channels a signal from the attachment to the handle for indicating the status of the attachment (for example, whether a clamping function is holding). Similarly, a second electrical lead may be provided to supply power to separate aspects of the attachment if so required (for example, as will be described more fully with respect to one embodiment of the linear stapling attachment, the use of a selectively engageable electromagnetic seal for ensuring continued clamping through the stapling process may be provided and require power selectively provided from the handle's power supply).

More particularly, with respect to the linear clamping, cutting, and stapling attachment, which has several different potential embodiments, two of which are disclosed herein as examples, the attachment is fitted with two drive extensions, which in operation function as extensions of the flexible drive shafts of the electromechanical driver. That is, when the attachment is mated to the electromechanical driver, the drive extensions are in mechanical communication with the flexible drive shafts such that the activation of the drive shaft motors activates the drive extensions within the linear clamping, cutting and stapling attachment. In each embodiment of the attachment, the first drive extension enables a linear clamping mechanism, while the second drive extension enables a cutting and stapling mechanism. In one embodiment, the linear clamping mechanism comprises a scissors-cuff system whereby the upper jaw of the scissors is clamped to the lower jaw of the scissors as a cuff enclosing a length of the scissors is moved from the hinged end of the scissors toward the closing end of the scissors. The scissors can be unclamped as the cuff is returned to its original position. In this embodiment, the first drive extension moves the cuff forward or backward, depending on the turning direction of the corresponding motor in the electromechanical driver. In a second embodiment, the linear clamping mechanism comprises a separating jaw system whereby an upper jaw is raised and subsequently lowered to meet a lower jaw to effect a clamping. In this embodiment, the first drive extension engages a pair of threaded vertical shafts which raise or lower the upper jaw depending on the turning direction of the corresponding motor in the electromechanical driver. In each of these embodiments, when the jaws are closed, a pair of sensor electrodes disposed on the jaws come into contact and thereby complete a sensor circuit which alerts the surgeon that it is safe or appropriate to activate the stapling mechanism and/or automatically activates the stapling mechanism.

In each of these embodiments, the stapling mechanism of the present invention comprises a replaceable tray of open staples set within the lower jaw and a set of corresponding staple guides fitted on the upper jaw, such that when the linear clamping mechanism is in a closed position, the open staples immediately oppose the corresponding staple guides. The stapling mechanism further comprises a blade for cutting through the bowel tissue head between the jaws. This mechanism comprises a wedge pushing system whereby once the linear clamping mechanism is in a closed position, a wedge riding in a channel below the tray of open staples is pushed through the channel. As the wedge moves through the channel, a sloping surface of the wedge pushes the open staples against the corresponding staple guides, thereby closing the staples. The blade portion seats above this sloping surface and cuts through the bowel tissue. After the staples have been closed, the wedge is pulled back through the channel. The second drive extension pushes or pulls the wedge and blade mechanism through the channel, depending on the turning direction of the corresponding motor in the electromechanical driver, by engaging a threaded horizontal shaft upon which the wedge, having a matching inner thread, rides.

Referring now to the anastomosing and stapling attachment, a preferred embodiment is described hereinbelow as a single example of the different variations which could be constructed for the equivalent purpose. As with the linear stapling attachments described above, however, this example demonstrates the universal applicability of the overall electromechanical driver mechanism of the present invention. This attachment comprises an anvil portion, and a staple, blade and reservoir portion, which includes a pair of turning drive shafts which are coupleable to the drive components of the shaft element described above, and a corresponding pair of advancing and retracting nuts mounted to the turning drive shafts, but which are prevented from rotating and therefore linearly advance and retract along the shafts when they turn. The anvil portion is bullet shaped, having a blunt nosed top portion, a flat cutting support surface on the bottom, and a freely rotating coupling post extending axially from the bottom surface. This coupling post is designed to be selectively coupleable and removable from the corresponding nut mounted to one of the turning drive shafts. The staple, blade, and reservoir portion (SBR portion) is cylindrical in shape, forming a housing which has a hollow interior. It is this hollow interior which forms the reservoir. On the axially outward facing surface of the cylindrical wall of the housing are a series of staple ports, through which the staples of the device are discharged. A series of staple drivers are mounted within the cylindrical walls, beneath the staple ports, for driving the staples therethrough. More accurately, the staple drivers are a series of protuberances on the outer edge of a single cylindrical component which seats in the wall of the SBR portion. The staples, prior to being discharged, are mounted in the holes; and they are advanced through the holes by the forward motion of the staple driver and the protuberances thereof. The blade is similarly cylindrical, and seats in the inside of the housing, against the inner surface of the wall thereof. Both the blade and the staple driver are mounted to the second nut, which is, in turn, mounted to the other turning drive shaft. As the turning drive shaft rotates, the nut (which is constrained against rotating) advances along the shaft, thus linearly advancing the blade and staple driver. The blade and the staple driver are, therefore, selectively advanceable axially outward from the housing, in accordance with actuation of the appropriate trigger on the handle. In practice, this attachment is utilized, once the section of the colon which is to be removed has been resected (but prior to completing the linear clamping and stapling step), in the following manner. The surgeon begins by coupling the anastomosing and stapling attachment to the electromechanical driver and advancing the anvil portion to its fullest extent. The anvil head is then removed and inserted into the exposed proximal end. As described above, this proximal end is then stapled closed. The surgeon then advances the shaft and the SBR portion of the attachment up the colon until it extends through the stapled distal end of the colon. The surgeon then couples the anvil to the advancing and retracting nut of the corresponding drive shaft. Subsequent triggering of the motor in the handle causes the anvil to retract toward the SBR portion. In a preferred embodiment, the base of the anvil and the outer edge of the SBR housing comprise an electromagnetic sensor which is coupled to the LCD indicator of the handle, thereby permitting the surgeon to know when the anvil and the SBR have come close enough to drive the blade and staples. Subsequent actuation of the other trigger on the handle causes the corresponding other turning drive shaft to advance the blade and staple driver into contact with the opposing face of the anvil. The blade cuts through the stapled-closed ends of the colon, leaving the tissue which has been severed in the interior reservoir. Simultaneously with the cutting, the freshly opened ends are joined together by the series of staples which are advanced through holes in the perimeter edge of the SBR (being pressed against and closed by the opposing face of the anvil). The attachment and the flexible shaft are then withdrawn from the patient.

BRIEF DESCRIPTION OF THE DRAWINGS

FIGS. 1 and 2 are side views of the closed and open dispositions, respectively, of a linear clamping, cutting and stapling attachment which is an aspect of the present invention;

FIGS. 5-12 are rear views in various cutaway planes of the linear clamping, cutting and stapling attachment shown in FIGS. 1-4 which is an aspect of the present invention;

FIGS. 13-17 are bottom, top cutaway, deep top cutaway, bottom cutaway, and top views, respectively, of the linear clamping, cutting and stapling attachment shown in FIGS. 1-12 which is an aspect of the present invention;

DETAILED DESCRIPTION OF THE PREFERRED EMBODIMENTS

Figure 3:
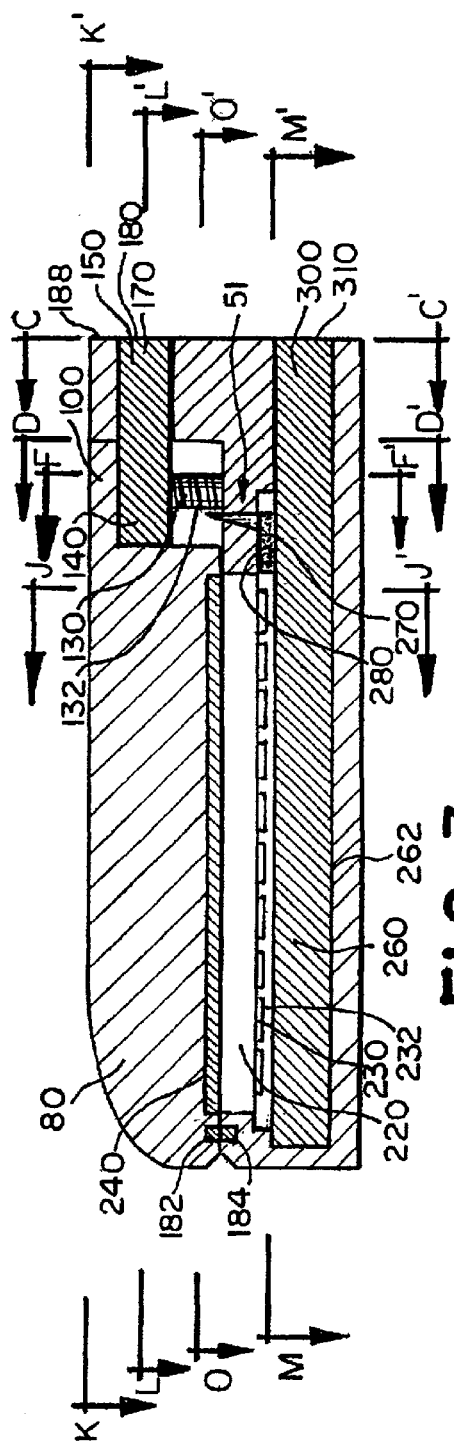
FIGS. 3 and 4 are cutaway side views of the closed and open dispositions, respectively, of the linear clamping, cutting and stapling attachment shown in FIGS. 1-2 which is an aspect of the present invention.
Figure 4:
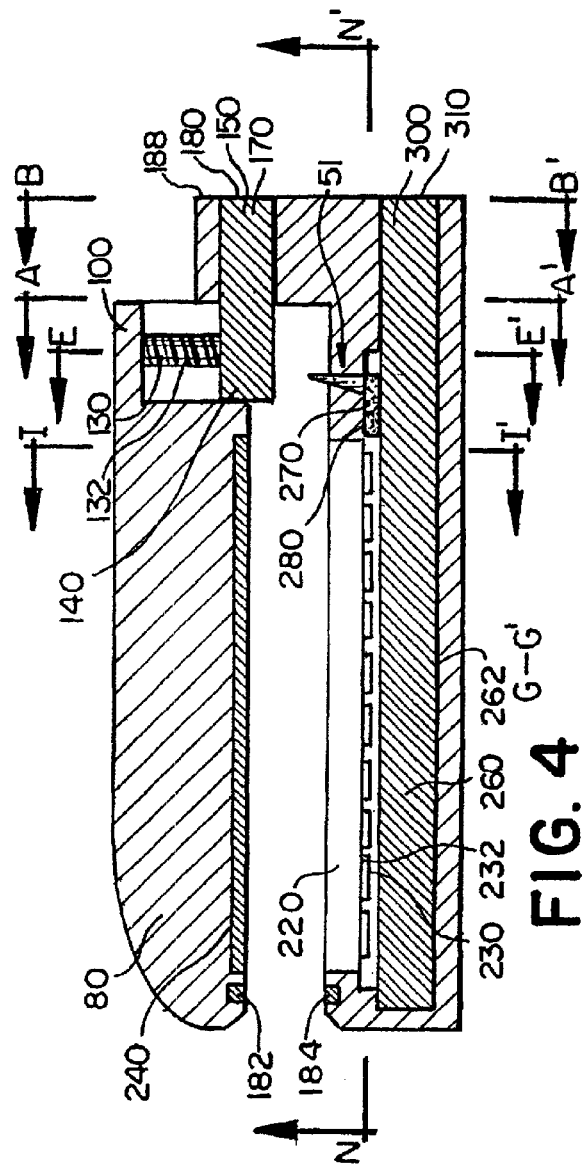

A preferred embodiment of the stapling mechanism of the linear clamping and stapling attachment according to the present invention is illustrated in FIGS. 1-18. More particularly, referring now to FIGS. 1, 2 and 13, a linear clamping mechanism and a stapling and cutting mechanism according to the present invention are shown as part of a linear clamping, cutting and stapling attachment 20. Referring now also to FIGS. 3 and 4, in this preferred embodiment, the linear clamping mechanism comprises a separating jaw system comprising a lower jaw 50 and an upper jaw 80 having a proximal end 100. Referring now also to FIGS. 7, 11, 14 and 17, the proximal end 100 of the upper jaw 80 has a pair of threaded vertical bores 90, through which extend a corresponding pair of vertical shafts 130. Inner threads 92 of the vertical bores 90 match outer threads 132 of the vertical shafts 130. Referring now also to FIGS. 6 and 10, the vertical shafts 130 engage a threaded upper horizontal shaft 150 at a distal end 140 of the upper horizontal shaft 150. Outer threads 152 of the upper horizontal shaft 150 interlock with the outer threads 132 of the vertical shafts 130. Referring now to FIGS. 3-5 and 9, the upper horizontal shaft 150 has at a proximal end 170 an upper drive socket 180. Referring to FIGS. 3-6, 9, 10, 14 and 17, the linear clamping mechanism further comprises a first sensor electrode 182 electrically communicating via communication wires (not shown) with a first contact pad 187 (best shown in FIGS. 6, 10, 14 and 17) which in turn electrically communicates with a second contact pad 189 (best shown in FIGS. 14 and 17) via direct contact, which electrically communicates via communication wires (not shown) with a first contact node 188 (best shown in FIGS. 5, 9 and 13). Similarly, the linear clamping mechanism further comprises a second sensor electrode 184 electrically communicating via communication wires (not shown) with a second contact node 186 (best shown in FIGS. 5, 9 and 13).

The contact nodes 186,188 electrically communicate with communication wires (not shown) in the electromechanical drive component (not shown) to form a sensor circuit, such that when the upper jaw 80 and the lower jaw 50 are clamped together, the sensor electrodes 182, 184 are in contact, the sensor circuit is closed, and the surgeon is alerted via other circuit components (not shown) to the clamped position of the jaws 50, 80, and is therefore informed that it is safe and/or appropriate to active the stapling mechanism.

Further in this preferred embodiment, and referring now to FIGS. 3, 4, 8, 12, 16 and 18, the cutting and stapling mechanism comprises a wedge pushing system comprising in the lower jaw 50 a replaceable tray 220 housing one or more fastening rods, or staples 230, and in the upper jaw 80 one or more staple guides 240 corresponding to the staples 230. Each of the staples 230 has a butt 232 protruding below the tray 220, and a pair of prongs 234 extending to the top of the tray 220. Referring now also to FIGS. 7, 11 and 15, the wedge pushing system further comprises a wedge guide, or channel 250 extending beneath the tray 220. Within the channel 250 extends a threaded lower horizontal shaft 260 having outer threads 262. Upon the lower horizontal shaft 260 travels a wedge 270 having a sloped top face 280, a horizontal threaded bore 290 (best shown in FIGS. 7 and 11) coaxial with the channel 250, having and inner threads 292 matching the outer threads 262 of the lower horizontal threaded shaft 260, and an upwardly extending blade member 51. Referring now to FIGS. 3, 4, 5 and 9, the lower horizontal shaft 260 has at a proximal end 300 a second drive socket In operation, after the surgeon has located the cancerous or anomalous tissue in the gastrointestinal tract, the patient's abdomen is initially opened to expose the bowel. The surgeon then cuts the tube of the bowel on either side of the cancerous tissue, thereby creating two open ends of the bowel, a distal end which is directed toward the anus, and a proximal end which is closest to the lower intestine. In order to minimize contamination, the surgeon then uses the linear clamping, cutting and stapling attachment to temporarily staple the exposed ends. According to the clamping, cutting and stapling procedure described below, the proximal and distal ends of the bowel will be clamped, cut, and stapled.

Figure 3A:
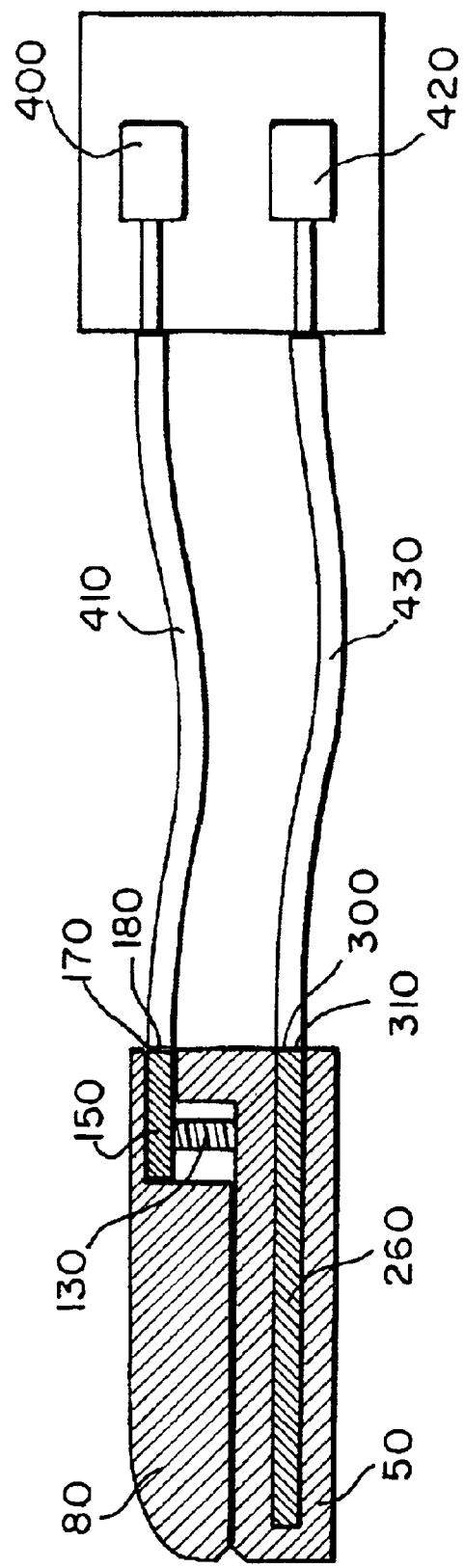
FIG. 3A is another cutaway view of the closed disposition of the linear clamping, cutting and stapling attachment shown in FIGS. 1-4, which is an aspect of the present invention.
Figure 18:
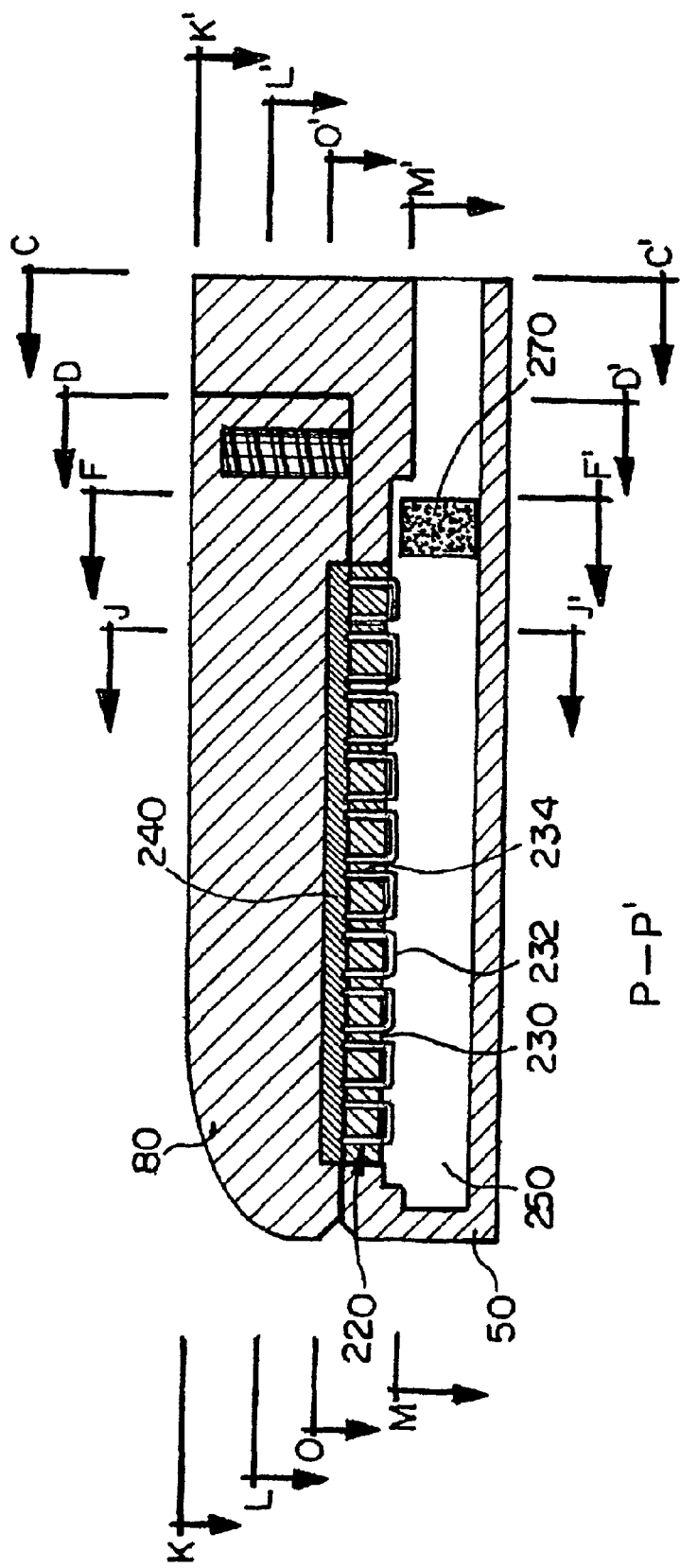
FIG. 18 is a side cutaway of the linear clamping, cutting and stapling attachment shown in FIGS. 1-17 which is an aspect of the present invention.
Figure 19:
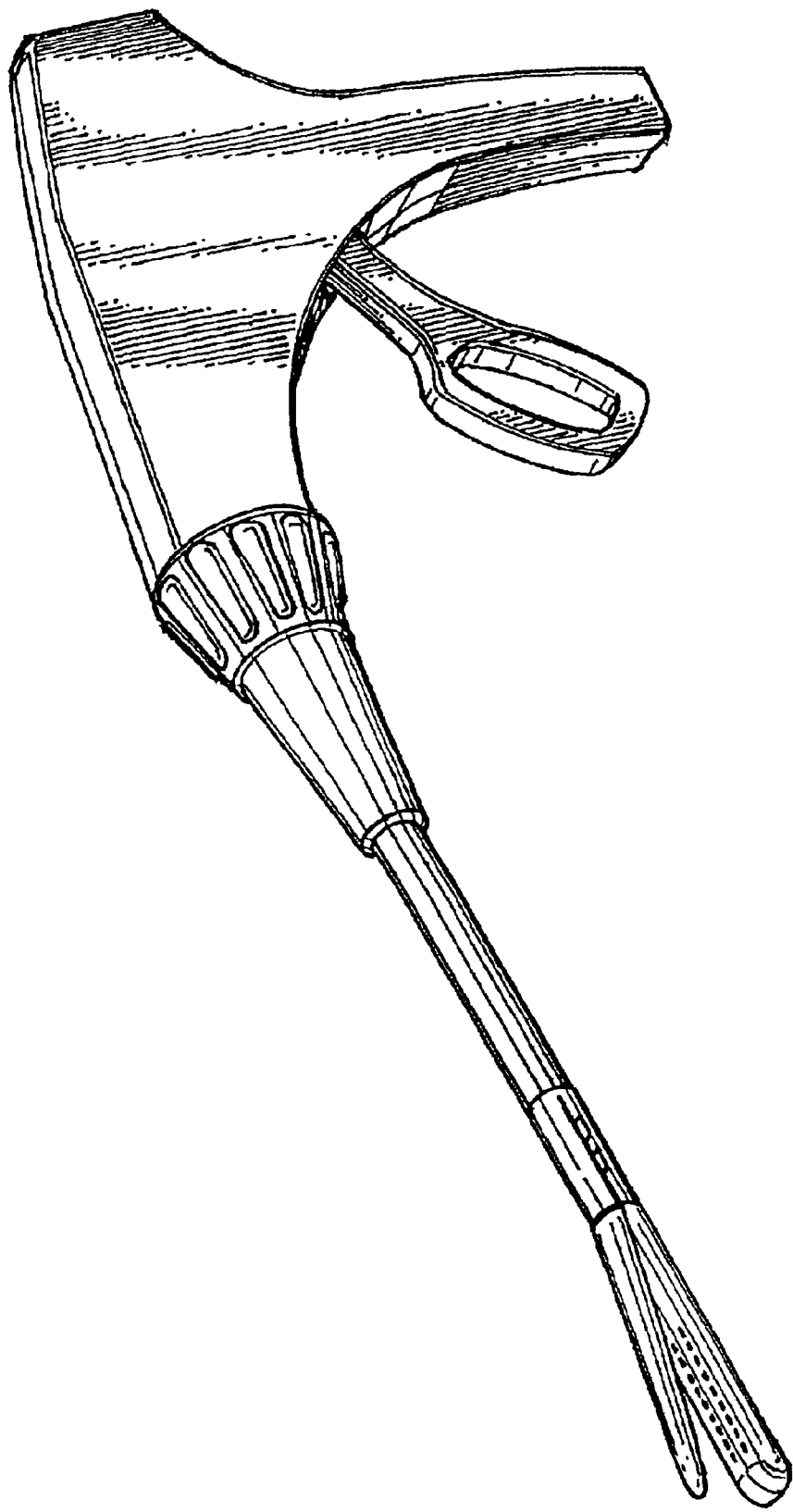
FIG. 19 is a perspective view of a linear clamping, cutting and stapling mechanism of the prior art.
Figure 20:
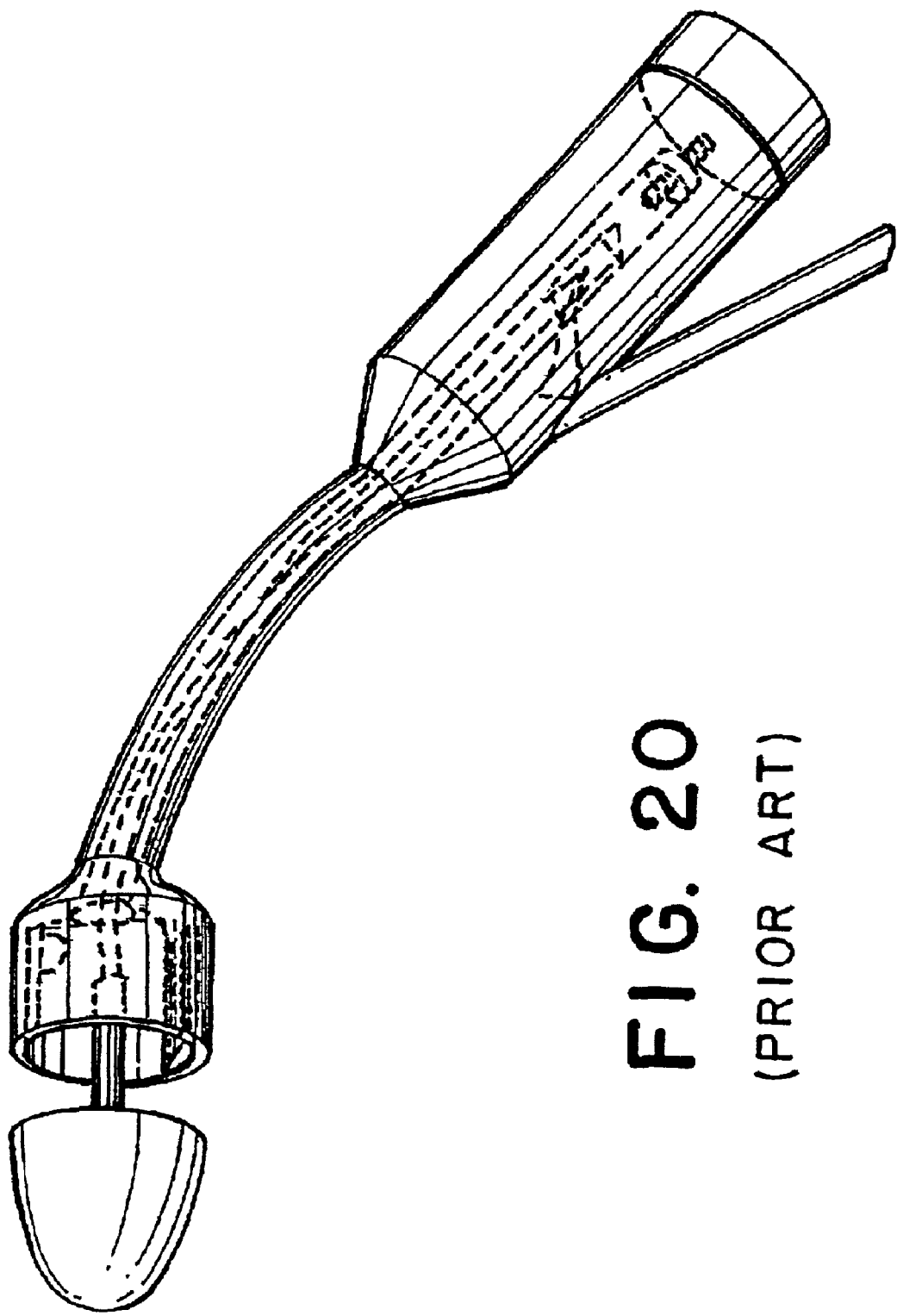
FIG. 20 is a perspective view of an anastomosing and stapling mechanism of the prior art.

More particularly, referring to FIG. 3A, the linear clamping, cutting and stapling attachment is mated to the attachment socket of the electromechanical driver component such that the upper drive socket 180 engages the corresponding flexible drive shaft 410 of the electromechanical driver component and the second drive socket 310 engages the corresponding flexible drive shaft 430 of the electromechanical driver component. Thus, rotation of the upper horizontal shaft 150 is effected by rotation of the upper drive socket 180 which is effected by rotation of the corresponding flexible drive shaft 410 of the electromechanical driver component. Clockwise or counter-clockwise rotation is achieved depending on the direction of the responsible motor 400. Similarly, rotation of the lower horizontal shaft 260 is effected by rotation of the second drive socket 310 which is effected by rotation of the corresponding flexible drive shaft 430 of the electromechanical driver component. Again, clockwise or counter-clockwise rotation is achieved depending on the direction of the responsible motor 420.

In order to clamp the exposed ends of the bowel, the surgeon first activates the upper motor 400 corresponding to the upper flexible drive shaft 410 which engages the upper drive socket 180 at the proximal end 170 of the upper horizontal shaft 150, thereby causing the upper horizontal shaft 150 to turn in a clockwise rotation. When the linear clamping and stapling attachment is in an initial closed state as shown in FIG. 1, this clockwise rotation of the upper horizontal shaft 150 causes the outer threads 152 of the upper horizontal shaft 150 to engage the outer threads 132 of the vertical shafts 130, thereby causing the vertical shafts 130 to turn in a clockwise rotation. This clockwise rotation of the vertical shafts 130 causes the outer threads 132 of the vertical shafts 130 to channel within the inner threads 92 of the vertical bores 90, thereby causing the upper jaw 80 to rise and begin separating from the lower jaw 50. Continuous operation of the motor in this manner eventually places the linear clamping and stapling attachment in an open state, providing a space between the upper jaw 80 and the lower jaw 50, as shown in FIG. 2. Once the linear clamping and stapling attachment is in this open state, the surgeon has access to the tray 220 of staples 230, and can check to ensure that the staples 230 are ready for the procedure and/or replace the tray 220 with a more suitable tray 220, as shown in FIG. 16. Once the surgeon has verified that the tray 220 is ready and in place, the surgeon places the open distal end of the colon between the upper jaw 80 and lower jaw 50. Thereafter, the surgeon reverses the upper motor 400 to effect a counter-clockwise rotation of the upper horizontal shaft 150, which in turn effects counter-clockwise rotation of the vertical shafts 130, which in turn effects a lowering of the upper jaw 80. Continuous operation of the upper motor 400 in this manner eventually returns the linear clamping and stapling attachment to a closed state, where the distal end of the bowel is clamped between the upper jaw 80 and the lower jaw 40, with a small portion of the distal end of the bowel extending laterally beyond the upper jaw 80 and the lower jaw 50.

Once the distal end of the bowel is clamped as described above, the sensor electrodes 182, 184 are in contact, and the surgeon is alerted via circuit components in the electromechanical drive component that it is safe and/or appropriate to activate the stapling mechanism. The surgeon then activates the stapling mechanism. It should be noted that the resistance afforded by the mechanical relationships between the upper jaw 80, vertical bores 90, vertical shafts 130, horizontal shaft 150, and upper drive socket 180 of the linear clamping and stapling attachment, and the upper flexible drive shaft 410 and upper motor 400 of the electromechanical driver component, together ensure that the upper jaw 80 and lower jaw 50 remain clamped together during the operation of the stapling mechanism. To begin the stapling and cutting procedure, the surgeon activates the lower motor 420 of the electromechanical driver component corresponding to the lower flexible drive shaft 430 which engages the lower drive socket 310 at the proximal end 300 of the lower horizontal shaft 260, thereby causing the lower horizontal shaft 260 to turn in a clockwise rotation. When the stapling and cutting mechanism is in an initial loaded state, the wedge 270 and the blade 51 associated therewith are in the channel 250 at a position closest to the proximal end 300 of the lower horizontal shaft 260, as shown in FIGS. 3 and 4. The clockwise rotation of the lower horizontal shaft 260 causes the outer threads 262 of the lower horizontal shaft 260 to engage the inner threads 292 of the horizontal threaded bore 290 of the wedge 270, thereby causing the wedge 270 to travel through the channel 250 in a direction away from the proximal end 300 of the lower horizontal shaft 260. Continuous operation of the lower motor 420 in this manner will move the wedge 270 fully through the channel 250. As the wedge 270 moves through the channel, the blade 51 mounted to the top of the wedge cuts through the bowel, transecting it. Simultaneously, the sloped top face 280 of the wedge 270 contacts the butts 232 of the staples 230, thereby pushing the prongs 234 of the staples 230 through the tissue of the clamped distal end of bowel and against the staple guides 240, which bends and closes the staples 230. When the wedge 270 is moved fully through the channel 250, all of the staples 230 are pushed through the tray 220 and closed, thereby stapling closed the distal end of the bowel. Thereafter, the surgeon reverses the lower motor 420 to effect a counter-clockwise rotation of the lower horizontal shaft 260, which in turn moves the wedge 270 toward the proximal end 300 of the lower horizontal shaft 260. Continuous operation of the lower motor 420 in this manner eventually returns the wedge 270 to its initial position.

Thereafter, the surgeon again activates the upper motor 400 to effect a clockwise rotation of the upper horizontal shaft 150, which in turn effects a clockwise rotation of the vertical shafts 130, which in turn effects a raising of the upper jaw 80. Continuous operation of the upper motor 400 in this manner eventually places the linear clamping, cutting and stapling attachment into an open state. Thereafter, the surgeon replaces the empty tray 220 with a full tray 220, and performs the same clamping, cutting and stapling procedure on the proximal end of the bowel. Once the proximal end of the bowel is also clamped, cut and stapled, the surgeon may separate the attachment from the electromechanical driver component, discard the attachment, and use the electromechanical driver component for additional procedures with other attachments.

These and other advantages of the present invention will be apparent to those skilled in the art from the foregoing specification. Accordingly, it will be recognized by those skilled in the art that changes or modifications may be made to the above-described embodiments without departing from the broad inventive concepts of the invention. It should therefore be understood that this invention is not limited to the particular embodiments described herein, but is intended to include all changes and modifications that are within the scope and spirit of the invention as set forth in the claims.

What is claimed is:

1. A device for cutting and fastening a section of tissue, comprising:

a first jaw;

a second jaw in opposed correspondence with the first jaw and adapted to retain one or more fasteners, the first and second jaws being movable in a non-rotational manner relative to one another between an open position and a closed position;

a wedge, disposed in an axially translating relation at the second jaw, the wedge including a blade and a sloped surface, such that during the selective axial translation of the wedge, the blade transects the section of tissue, and the sloped surface drives the fasteners through the tissue and toward the first jaw, thereby fastening the section;

a first rotatable shaft for effecting the relative movement of the first and second jaws between the open position and the closed position; and a second rotatable shaft for driving the wedge member, the second rotatable shaft being rotatable independently of the first rotatable shaft.

2. The device of claim 1, comprising a wedge guide integral with the second jaw, the wedge translating along the wedge guide.

3. The device of claim 2, wherein the wedge guide has a linear axis and a wall, and wherein the wedge has an outer surface, and wherein interaction between the outer surface and the wall prevents rotation of the wedge about the linear axis of the wedge guide, and wherein the wedge has a threaded bore having a cylindrical axis coaxial with the linear axis of the wedge guide and having inner threads, and wherein the second rotatable shaft comprises a threaded shaft having outer threads and extending along the wedge guide and having a cylindrical axis coaxial with the cylindrical axis of the bore, the inner threads of the bore mating with the outer threads of the threaded shaft, wherein a rotation of the threaded shaft about the cylindrical axis of the bore causes the outer threads to ride along the inner threads, causing the wedge to travel along the shaft and along the wedge guide.

4. The device of claim 3, wherein the wedge guide includes a linear channel having a cross-section, and wherein the wedge has a cross-section substantially matching the cross-section of the channel.

5. The device of claim 4, wherein the first jaw has a first surface, and wherein the second jaw has a second surface in opposed correspondence to the first surface of the first jaw, and wherein each of the fasteners has a butt and at least one prong, and wherein the butt protrudes into the channel, and wherein each prong extends to the second surface of the second jaw, such that when the sloped surface of the wedge contacts each butt, each prong is pushed through the second surface of the second jaw, and such that when each prong is so pushed through the second surface of the second jaw, and the first surface of the first jaw and the second surface of the second jaw are substantially adjacent, each prong contacts the first surface of the first jaw.

6. The device of claim 5, wherein one or more of the fasteners are staples, and wherein the first surface of the first jaw includes one or more staple guides corresponding to the prongs of the staples, each staple guide forming a pair of concave pockets adapted to receive the prongs of the staples and thereafter guide the prongs toward a bent closed position.

7. The device of claim 6, comprising a removable staple tray housing the staples, and wherein the second surface of the second jaw is adapted to receive the removable staple tray.

8. The device of claim 3, wherein the threaded shaft has a proximal end mechanically communicating with a means for rotating the threaded shaft.

9. The device of claim 8, wherein the means is a motor.

10. The device of claim 9, wherein the motor has a drive extension having a distal end, and wherein the proximal end of the threaded shaft has a drive socket adapted to receive the distal end of the drive extension.

11. The device of claim 8, wherein one of a clockwise rotation and a counterclockwise rotation of the threaded shaft causes the wedge to travel away from the proximal end of the threaded shaft, and wherein the other of the clockwise rotation and the counter-clockwise rotation of the threaded shaft causes the wedge to travel toward the proximal end of the threaded shaft.

12. The device of claim 3, wherein the threaded bore of the wedge is a threaded channel.

13. The device of claim 1, including a sensor for sensing when the first jaw is adjacent to the second jaw.

14. The device of claim 13,
wherein the sensor includes a first electrical contact on the first jaw and a second electrical contact on the second jaw, each of the first and second electrical contacts being in electrical communication with a proximity sensing circuit such that when the first and second electrical contacts are touching, the proximity sensing circuit is closed.

15. A device for cutting and fastening a section of tissue, comprising:
a first jaw;
a second jaw in opposed correspondence with the first jaw and adapted to retain one or more fasteners, the first and second jaws movable in a non-rotational manner relative to one another between an open position and a closed position for retaining the tissue therebetween;
a blade for linearly cutting the section of tissue and a staple driver for driving the fasteners through the tissue and toward the first jaw;
a first rotatable shaft for effecting the relative movement of the first and second jaws between the open position and the closed position; and
a second rotatable shaft for driving the blade and the staple driver.

16. The device according to claim 15, wherein the second rotatable shaft has outer threads for driving the blade and the staple driver.

17. The device according to claim 16, wherein the second rotatable shaft is adapted to drive the staple driver and the blade simultaneously.

18. The device according to claim 16, comprising a first motor for driving the first rotatable shaft and a second motor for driving the second rotatable shaft.

19. The device according to claim 16, comprising a motor arrangement for driving each of the first rotatable shaft and the second rotatable shaft.

20. The device according to claim 16, wherein each of the first and second rotatable shafts includes a drive socket for engaging an end of a respective drive shaft.

21. The device according to claim 15, wherein the first jaw and the second jaw are maintained in a substantially parallel relationship between the open position and the closed position.

22. A device for cutting and fastening a section of tissue, comprising:
a first jaw;
a second jaw in opposed correspondence with the first jaw and adapted to retain one or more fasteners, the first and second jaws movable in a non-rotational manner relative to one another between an open position and a closed position for retaining the tissue therebetween;
a blade for linearly cutting the section of tissue and a staple driver for driving the fasteners through the tissue and toward the first jaw;
a first rotatable shaft for effecting the relative movement of the first and second jaws between the open position and the closed position; and a wedge disposed in an axially translating relation along the second jaw, the wedge including the blade and the staple driver, the wedge having a sloped surface, such that during selective axial translation of the wedge, the blade transects the section of tissue and the sloped surface drives the fasteners through the tissue toward the first jaw.

23. A device for cutting and fastening a section of tissue, comprising:
a first jaw:
a second jaw in opposed correspondence with the first jaw and adapted to retain one or more fasteners, the first and second jaws movable in a non-rotational manner relative to one another between an open position and a closed position for retaining the tissue therebetween;
a blade for linearly cutting the section of tissue and a staple driver for driving the fasteners through the tissue and toward the first jaw; and
a first rotatable shaft for effecting the relative movement of the first and second jaws between the open position and the closed position,
wherein the second jaw includes a wedge guide and wherein the staple driver includes an axially translatable wedge adapted to translate along the wedge guide.

24. A device for cutting and fastening a section of tissue, comprising:
a first jaw;
a second jaw in opposed correspondence with the first jaw and adapted to retain one or more fasteners, the first and second jaws being movable in a non-rotational manner relative to one another between an open position and a closed position for retaining the tissue therebetween;
a first rotatable shaft having a longitudinal axis;
a blade driven by the first rotatable shaft, said blade adapted for cutting the tissue along a path parallel to a plane containing the longitudinal axis of the first shaft; and
a staple driver driven by the first rotatable shaft, said staple driver adapted for driving the fasteners through the tissue and toward the first jaw.

25. The device according to claim 24, wherein the second rotatable shaft has outer threads for effecting the relative movement of the first and second jaws between the open position and the closed position.

26. The device according to claim 24, wherein the first rotatable shaft is adapted to drive the staple driver and the blade simultaneously.

27. The device according to claim 24, wherein the first jaw and the second jaw are maintained in a substantially parallel relationship between the open position and the closed position.

28. A device for cutting and fastening a section of tissue, comprising:
a first jaw:
a second jaw in opposed correspondence with the first jaw and adapted to retain one or more fasteners, the first and second jaws being movable in a non-rotational manner relative to one another between an open position and a closed position for retaining the tissue therebetween;
a first rotatable shaft having a longitudinal axis;
a blade driven by the first rotatable shaft, said blade adapted for cutting the tissue along a path parallel to a plane containing the longitudinal axis of the first shaft;
a staple driver for driving the fasteners through the tissue and toward the first jaw; and a wedge disposed in an axially translating relation along the second jaw, the wedge including the blade and the staple driver, the wedge having a sloped surface, such that during selective axial translation of the wedge, the blade transects the section of tissue and the sloped surface drives the fasteners through the tissue toward the first jaw.

29. A device for cutting and fastening a section of tissue, comprising:

a first jaw;

a second jaw in opposed correspondence with the first jaw and adapted to retain one or more fasteners, the first and second jaws being movable in a non-rotational manner relative to one another between an open position and a closed position for retaining the tissue therebetween;

a first rotatable shaft having a longitudinal axis;

a blade driven by the first rotatable shaft, said blade adapted for cutting the tissue along a path parallel to a plane containing the longitudinal axis of the first shaft; and a staple driver for driving the fasteners through the tissue and toward the first jaw;

wherein the second jaw includes a wedge guide and wherein the staple driver includes an axially translatable wedge adapted to translate along the wedge guide.

* * * * *